United States Patent
Ardans et al.

(10) Patent No.: US 7,892,428 B2
(45) Date of Patent: Feb. 22, 2011

(54) TRANSDUCER PROTECTOR

(75) Inventors: Thierry Ardans, Brussels (BE); Vincent Houwaert, Celles (BE)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 822 days.

(21) Appl. No.: 11/682,801

(22) Filed: Mar. 6, 2007

(65) Prior Publication Data

US 2008/0221499 A1  Sep. 11, 2008

(51) Int. Cl.
 *B01D 63/08* (2006.01)
(52) U.S. Cl. .............. 210/321.6; 210/321.75; 210/321.64; 210/348
(58) Field of Classification Search .............. 210/321.6, 210/321.75, 321.84, 348; 604/6.16
 See application file for complete search history.

(56) References Cited

U.S. PATENT DOCUMENTS

| | | | |
|---|---|---|---|
| 5,500,003 A | 3/1996 | Guala et al. | |
| 5,603,792 A | 2/1997 | Guala et al. | |
| 6,086,762 A | 7/2000 | Guala | |
| 6,346,084 B1 * | 2/2002 | Schnell et al. | 600/561 |
| 6,383,158 B1 | 5/2002 | Utterberg et al. | |
| 6,514,225 B1 | 2/2003 | Utterberg et al. | |
| 6,536,278 B1 | 3/2003 | Scagliarini | |
| 6,755,801 B2 | 6/2004 | Utterberg et al. | |
| 7,069,788 B2 | 7/2006 | Teugels | |
| 7,175,697 B2 | 2/2007 | Neri | |
| 2002/0007137 A1 | 1/2002 | Utterberg et al. | |
| 2004/0127785 A1 * | 7/2004 | Davidson et al. | 600/407 |
| 2004/0173516 A1 * | 9/2004 | Guala | 210/321.8 |
| 2004/0237785 A1 | 12/2004 | Neri | |
| 2005/0131332 A1 | 6/2005 | Kelly et al. | |
| 2005/0132826 A1 * | 6/2005 | Teugels | 73/866.5 |
| 2005/0279692 A1 * | 12/2005 | Caleffi | 210/321.6 |

FOREIGN PATENT DOCUMENTS

| | | |
|---|---|---|
| WO | WO0032104 A1 | 6/2000 |
| WO | WO2004082732 A2 | 9/2004 |
| WO | WO2005044339 A2 | 5/2005 |
| WO | WO2005068043 A1 | 7/2005 |
| WO | WO2006074429 A1 | 7/2007 |

* cited by examiner

*Primary Examiner*—John Kim
(74) *Attorney, Agent, or Firm*—K&L Gates LLP

(57) ABSTRACT

A transducer protector (TP) and a method for forming the transducer protector are disclosed. The transducer protector is operable in cooperation with a hemodialysis system, and may be mounted between a drip chamber and a pressure transducer. The transducer protector is mounted in an integrally-assembled housing which includes an inlet from the hemodialysis system or drip chamber, and an outlet to the pressure transducer. The transducer includes at least one hydrophobic membrane that is attached permanently to either a first connector, a second connector or a peripheral ring, the connectors integrally attached to each other to form the TP housing.

10 Claims, 12 Drawing Sheets

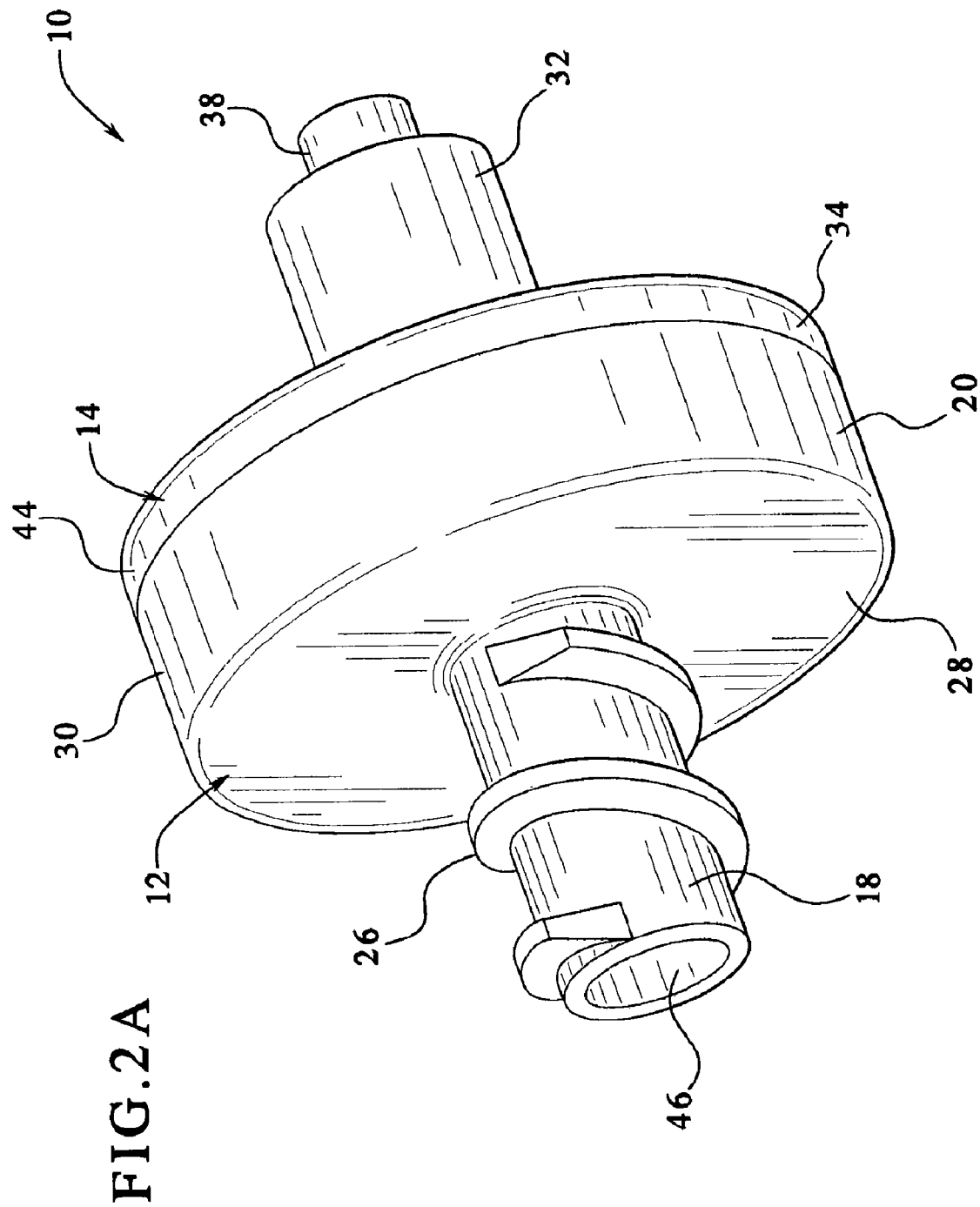

TRANSDUCER PROTECTOR

FIELD OF THE INVENTION

The present invention relates generally to medical treatments. More specifically, the present invention relates to a transducer protector for hemodialysis equipment.

BACKGROUND

Due to disease, insult or other causes, a person's renal system can fail. Renal failure causes several physiological complications. The balance of water and minerals, and the excretion of daily metabolic load are no longer possible in renal failure. During renal failure, toxic end products of nitrogen metabolism (e.g., urea, creatinine, uric acid, and others) can accumulate in blood and tissues.

Kidney failure and reduced kidney function have been treated with dialysis. Dialysis removes waste, toxins and excess water from the body that would otherwise have been removed by normal functioning kidneys. Dialysis treatment for replacement of kidney functions is critical to many people because the treatment is necessary to sustain the person's life. A person with failed kidneys cannot continue to live without replacing at least the filtration functions of the kidneys.

Two general types of dialysis therapy for treating patients with kidney failure are now in widespread use. One type, hemodialysis, provides for removing waste products by passing the blood of a patient through an appropriately constructed dialyzer unit located in an extracorporeal circuit. A second type of dialysis therapy, peritoneal dialysis, utilizes the membrane in a patient's peritoneal cavity for the purpose of separating waste products from the patient's fluid systems.

Hemodialysis treatment removes waste, toxins and excess water directly from the patient's blood. During the hemodialysis procedure, a trained health care professional will monitor the arterial and venous pressure of the patient in the extracorporeal circuit. Pressure is monitored in the extracorporeal circuit using a pressure transducer. Often, the transducer is placed at the end of a tube connected to a respective arterial or venous drip chamber. The pressure transducer measures air pressure, which is indicative of blood pressure. It is important that the blood not contact the air pressure transducer. One reason for this is to prevent cross-contamination between patients and provide a sterile barrier to reduce the risk of contamination by virus-infected blood in a liquid and/or aerosolized state. The barrier also filters particles, which might be entrained in an air stream and which could possibly be fed back to equipment within the dialysis machine.

Transducer protectors are made by assembling their constitutive parts, which may include a separation membrane and a housing for containing the membrane. One way of making transducer protectors is disclosed in U.S. Pat. No. 6,536,278. This patent discloses a transducer protector made from a membrane that is assembled to two housing halves. It is very important that there are no leaks of blood between the membrane and the housing in order to prevent transmission of the blood to the far side of the membrane and contamination of the pressure transducer. Assembling the transducer protector in this way does not allow for inspection of the seal between the membrane and the housing.

What is needed is a transducer protector to prevent contact between the blood and the transducer, thus preventing contamination of the transducer, and a better way to make the transducer protector. The transducer protector should be an in-line sterile barrier that can be placed between the transducer and the blood of the drip chamber to prevent blood or other liquid within the extracorporeal circuit from contaminating the pressure transducer.

SUMMARY

The present disclosure provides multiple embodiments for a transducer protector, and a method for forming the transducer protector, which is operable with a hemodialysis, hemofiltration, or hemodiafiltration system or machine, for example. The transducer protector in general is aligned between the extracorporeal circuit of the blood treatment machine and a pressure transducer, which gauges pressure within blood flowing through the circuit. The transducer protector is part of a disposable blood tubing set.

In one embodiment, a transducer protector is provided. The transducer protector includes a first connector having an inlet passageway for receiving at least one fluid, a second connector having an outlet passageway opposing the first passageway, the second connector being attached to the first connector, and a hydrophobic membrane integrally assembled with one of the first connector and the second connector, the hydrophobic membrane separating the inlet passageway from the outlet passageway, wherein the first and second connectors form an integrally-connected housing for protecting the hydrophobic membrane.

In another embodiment, a transducer protector for use in a blood treatment therapy is provided. The transducer protector includes a hydrophobic membrane molded to a peripheral ring, a first connector configured for connection to a first passageway, and a second connector configured for connection a second passageway, the first connector and the second connector integrally attached to the peripheral ring, wherein the hydrophobic membrane joins the first connector to the second connector.

In another embodiment, a method for making a transducer protector is provided. The method includes steps of providing a hydrophobic membrane, integrally assembling the hydrophobic membrane to a first plastic housing, and integrally assembling the hydrophobic membrane and first plastic housing in a separate step to a second plastic housing to form a transducer protector.

Another embodiment is a method for making a transducer protector. The method includes steps of providing a hydrophobic membrane and overmolding the hydrophobic membrane to a plastic housing in a single step to form a transducer protector.

An advantage of the present disclosure is accordingly to provide an improved transducer protector for blood treatment therapies. Another advantage is to provide a membrane integrally formed with the housing of the transducer protector to increase the integrity of the attachment between the membrane and the housing. Additional features and advantages are described herein, and will be apparent from, the following Detailed Description and the figures.

BRIEF DESCRIPTION OF THE FIGURES

FIG. 2A is a top perspective view of one embodiment of a transducer protector.

DETAILED DESCRIPTION OF THE PRESENTLY PREFERRED EMBODIMENTS

Figure 1:
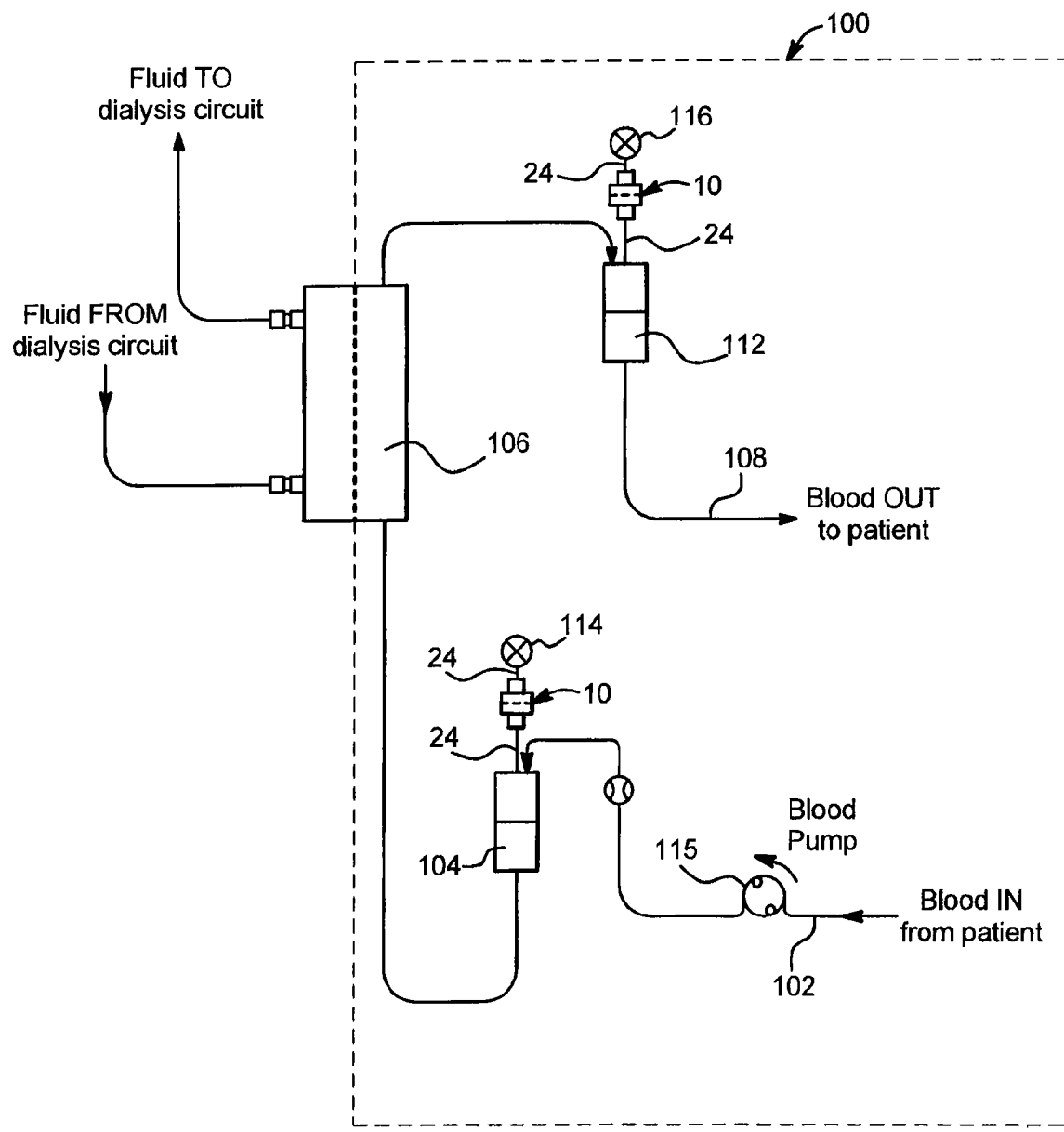
FIG. 1 is a schematic view of a blood circuit or extracorporeal circuit for a hemodialysis therapy showing one use or application of the transducer protector of the present disclosure.
Figure 2B:
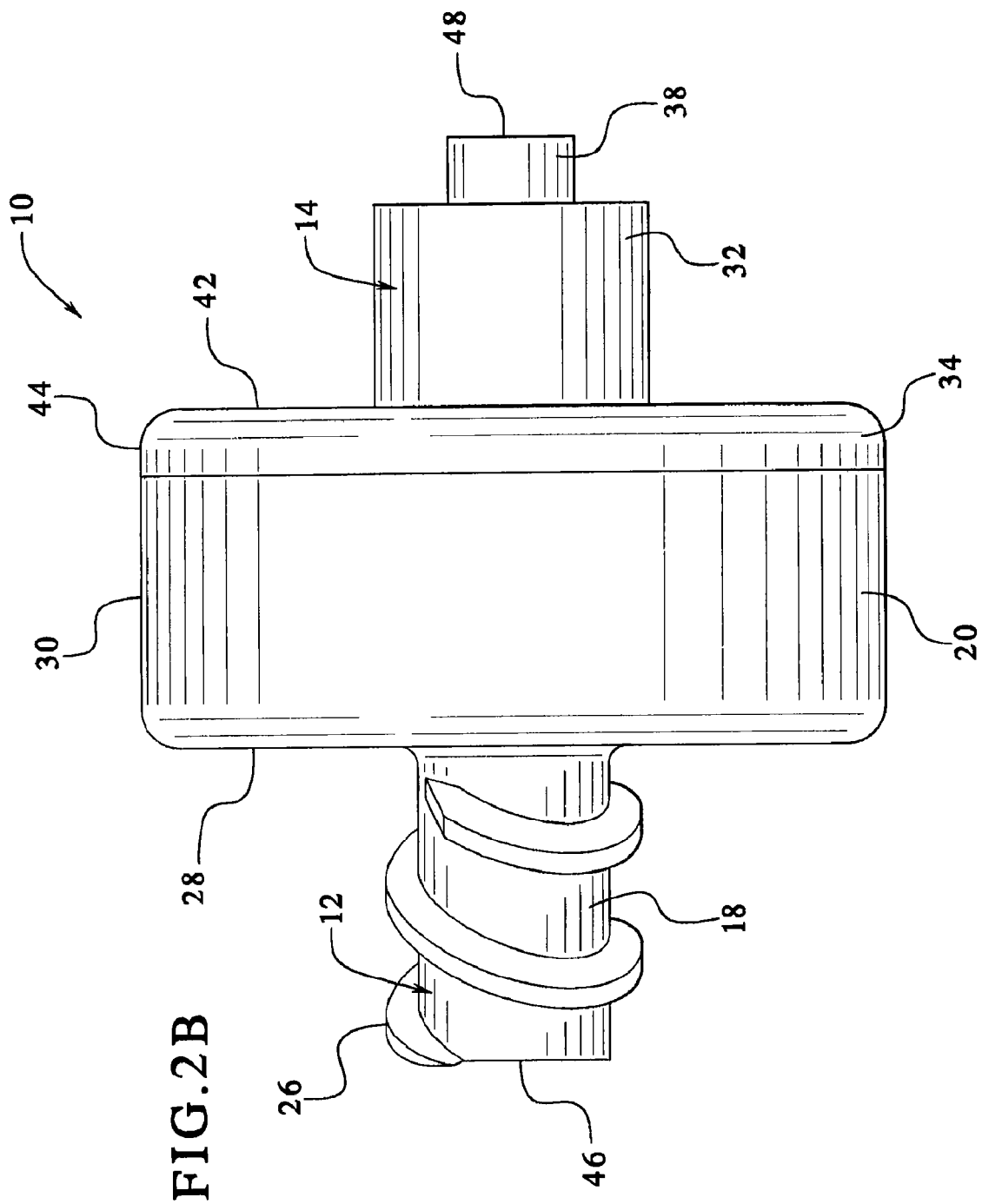
FIG. 2B is a side view of the transducer protector of FIG. 2A.

Referring to FIG. 1, an extracorporeal blood circuit 100 for performing hemodialysis therapy is shown. While hemodialysis is one suitable blood treatment for the transducer protector of the present disclosure, it should be appreciated that the transducer protector may be used for other types of fluid treatments such as hemofiltration and hemodiafiltration. The blood circuit 100 includes an arterial blood line 102 and an arterial drip chamber 104 through which blood is pumped via a blood pump 105 into a dialyzer 106 from a patient. The blood circuit 100 also includes a venous blood line 108 and a venous drip chamber 112 through which blood flows from the dialyzer 106 to the patient. The dialyzer 106 is connected to the blood circuit 100 and a dialysate circuit, wherein dialysis fluid circulates through the dialysate circuit and dialyzer to remove impurities from the blood.

The blood circuit 100 further includes an arterial pressure transducer 114 and a venous pressure transducer 116 for measuring the pressure of the blood flowing from and into the patient. Arterial pressure transducer 114 and venous pressure transducer 116 are each connected at the end of a tube 24, which extends from a top of the respective arterial drip chamber 104 and venous drip chamber 112. The tops of arterial and venous drip chambers 104 and 112 are filled with air that has eggressed from blood that has pooled in the drip chambers. The eggressed air is under pressure from the blood, which is under pressure from the blood pump 105. Pressure transducers 114, 116 accordingly measure the pressure of air, which is indicative of blood pressure.

For operational and safety reasons, it is important to prevent blood from contacting the arterial and venous pressure transducers 114, 116. Accordingly, a transducer protector 10 (or any of the other transducer embodiments described herein) is located in tubing 24 between each drip chamber 104, 112 and its corresponding pressure transducer 114, 116 to prevent blood or other fluids from contacting and contaminating the pressure transducers 114, 116.

Blood circuit 100 is generally a one-use disposable item, with the exception of the pressure transducers. Accordingly, it is desirable to make the tubing of arterial lines 102, 108, dialyzer 106, drip chambers 104, 112, and transducer protectors 10 as safe and as cost effectively as possible. Pressure transducers 114, 116 are not disposable, hence the need to protect the transducers. The blood circuit 100 should also be relatively easy to connect to the blood treatment instrument, e.g., in a center by a nurse or at home by the patient or caregiver. The transducer protectors described herein are relatively low cost and easy to handle when connecting the resulting blood circuit 100 to the dialysis machine or system.

Referring to FIGS. 2A, 2B, 3 and 4, one embodiment of a transducer protector of the present disclosure is illustrated by protector 10. The transducer protector 10 as discussed is used for example in a hemodialysis treatment, or any other procedure in which blood contamination must be prevented. The transducer protector 10 to this end provides a sterile barrier so that corresponding pressure transducers 114, 116 can be used over multiple treatments without cross-contamination between patients using the same hemodialysis transducers.

Figure 3:
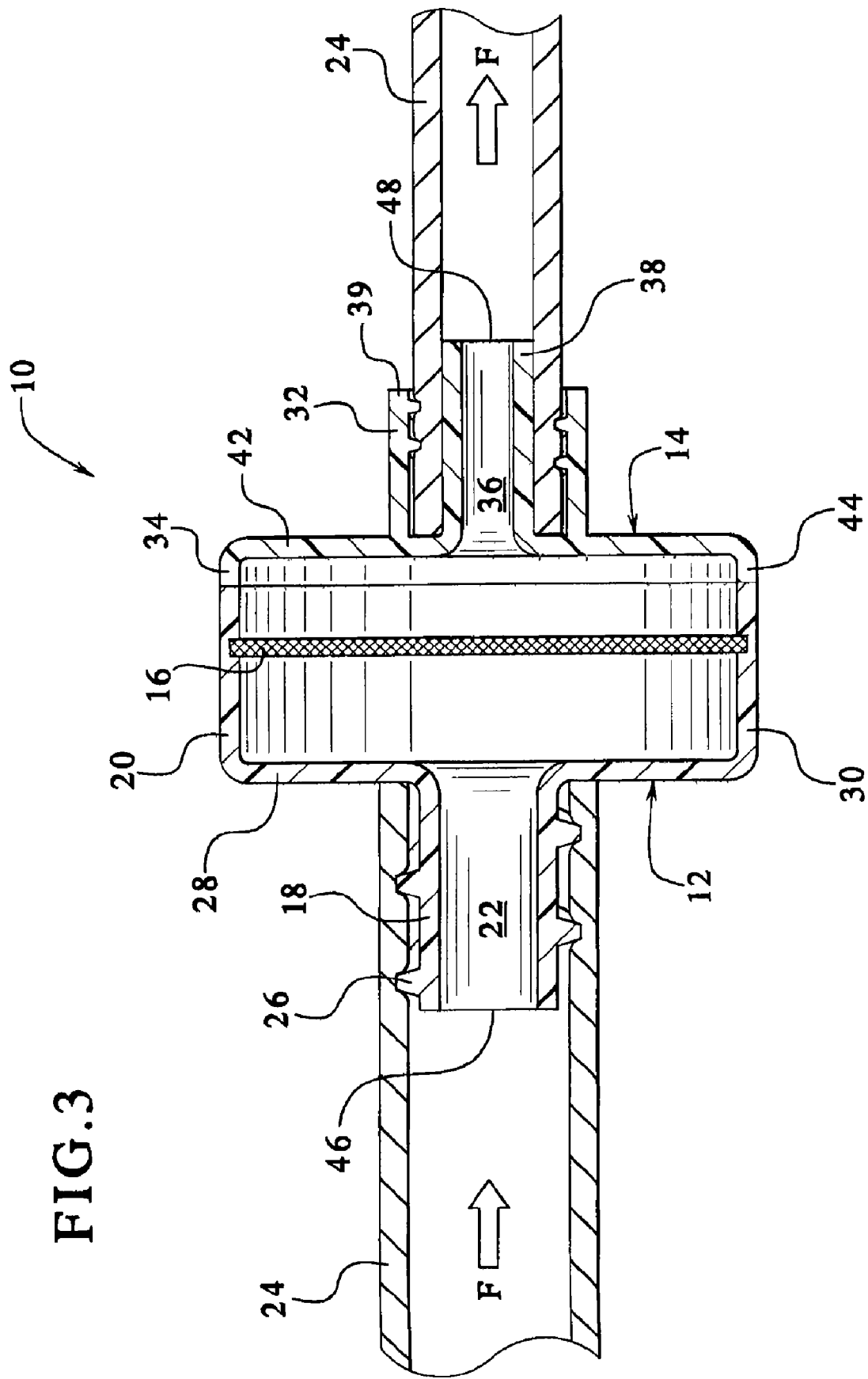
FIG. 3 is a cross-sectional view of another embodiment of a transducer protector.
Figure 4:
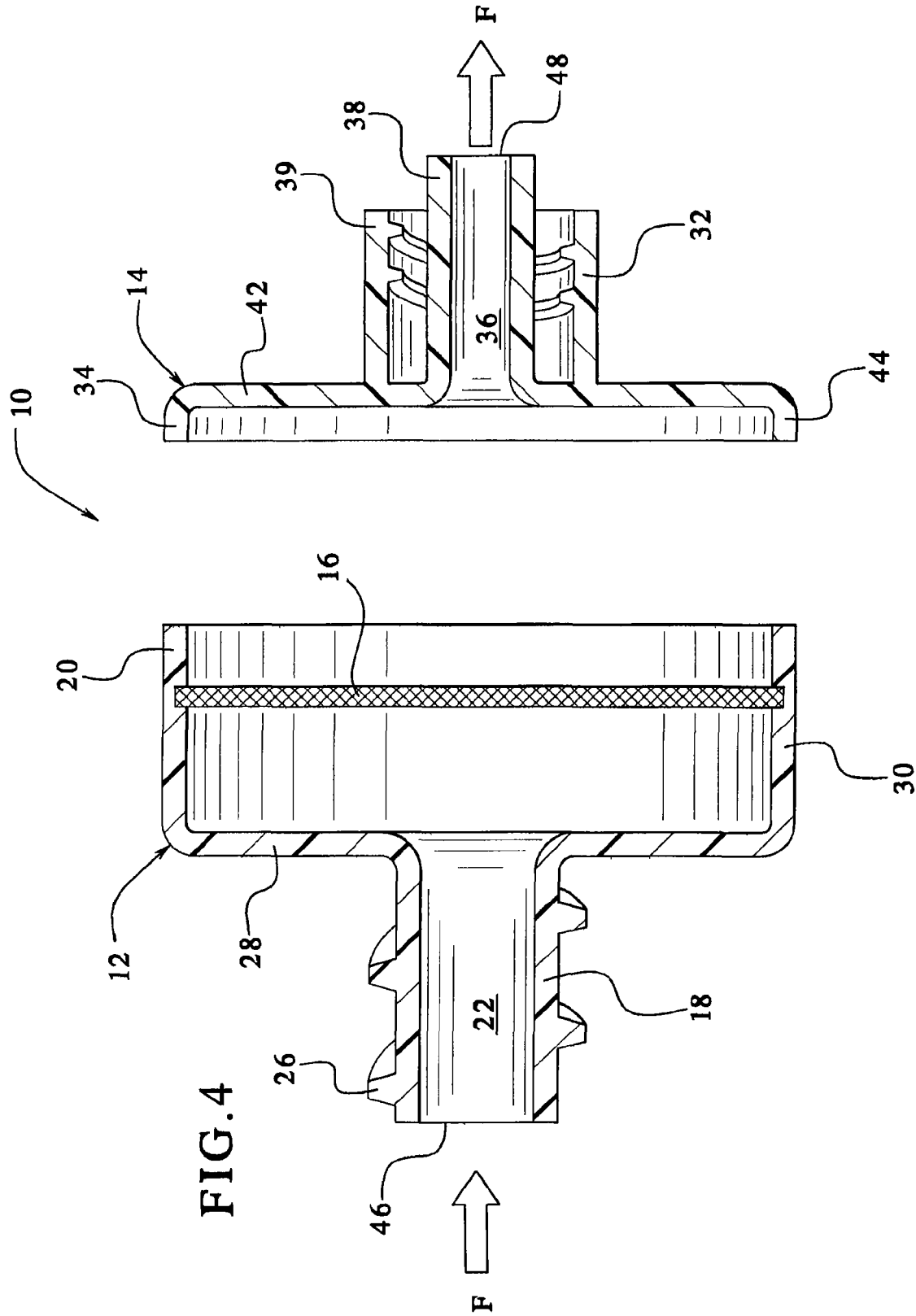
FIG. 4 is an exploded cross-sectional view of the transducer protector of FIG. 3.

As illustrated in FIGS. 3 and 4, an embodiment of a transducer protector 10 includes a housing having a first connector 12 and a second connector 14. A membrane 16 is also provided. The first and second connectors 12, 14 are formed of a moldable material that may be any one or more of, but is not limited to, polyvinylchloride (PVC), polyamide or nylon (PA), polycarbonate (PC), polyethylene (PE), polypropylene (PP), acrylonitrile-butadiene-styrene (ABS). In an embodiment, the first connector 12 is formed of the same material as the second connector 14. In another embodiment, the first connector 12 is formed of a different material than the second connector 12. The first connector 12 includes a first connecting mechanism 18, a first securing portion 20 and a first passageway 22. The first connecting mechanism 18 extends from the first securing portion 20 generally perpendicularly and has a generally tubular shape. The first connecting mechanism 18 is configured to releasably connect the first connector 12 to a tube 24 (FIG. 3) or any other passageway or conduit for transferring fluid through the transducer protector 10.

In an embodiment, the first connecting mechanism 18 includes a male luer lock having at least one thread 26 disposed on the outer surface thereof for a threaded connection to the tube 24. While the first connecting mechanism 18 is illustrated as a male luer lock, it should be understood by one skilled in the art that the first connecting mechanism 18 can alternatively use other securing mechanisms sufficient to securely connect the first connector 12 to a corresponding tube 24 or passageway including, but not limited to, a female luer lock, friction fit connector, protrusion-detent mechanism, keyed connector, or the like. The connection between the tube 24 and the first connector 12 should be a sealed connection, in which fluid or air cannot be introduced into the tube 24 or transducer protector 10 through the seal between the tube 24 and the first connector 12. The first connecting mechanism 18 is integrally formed with the first securing portion 20 of the first connector 12 in the illustrated embodiment.

In an embodiment, the first securing portion 20 of the first connector 12 extends from the first connecting mechanism 18 outwardly via a web 28 to a cylindrical flange 30, as shown in FIGS. 3 and 4. The illustrated web 28 extends radially from the first connecting mechanism 18 in a generally perpendicular manner. The illustrated flange 30 extends from the web 28 in a generally perpendicular manner, such that the flange 30 is aligned in a substantially parallel manner with the first connecting mechanism 18. The flange 30 forms a generally cylindrical body extending from the first connecting mechanism 18, but it should be understood by one skilled in the art that the flange 30 may be formed of any other shapes sufficient to provide a cavity therewithin through which a fluid passes. The first securing portion 20 and the first connecting mechanism 18 surround a first passageway 22 in a generally concentric manner.

In an embodiment, the first passageway 22 is formed in the first connector 12 and is in fluid communication with tube 24 which is attached to the first connecting member 18, as illustrated in FIGS. 3 and 4. The first passageway 22 extends inwardly from a distal end of the first connector 12. The diameter of the first passageway 22 in the illustrated embodiment is constant along the entire length of the first connecting mechanism 18, but it should be understood by one skilled in the art that the diameter may increase or decrease as desired as the first passageway 22 extends from the distal end of the first connector 12. The first passageway 22 extends through the first connecting mechanism 18 and the first securing portion 20 of the first connector 12.

In an embodiment, the first connector 12 is attached to the second connector 14, as shown in FIGS. 3 and 4. The second connector 14 includes a second connecting mechanism 32, a second securing portion 34, and a second passageway 36. The second connecting mechanism 32 extends from the second securing portion 34 in a generally normal manner. The second connecting mechanism 32 releasably connects the second connector 14 to a tube 24 (FIG. 3) or any other passageway or conduit for transferring fluid through the transducer protector 10. In an embodiment, the second connecting mechanism 32 is a female luer lock that includes a protrusion 38 and a clasp 39. The protrusion 38 and clasp 39 in the illustrated receive a tube 24 between the protrusion 38 and the clasp 39 such that the protrusion 38 secures the tube 24 therebetween to form a seal between the second connector 14 and the tube 24.

The second connecting mechanism 32 is integrally formed with the second securing portion 34 of the second connector 14. While the second connecting mechanism 32 is illustrated as a female luer lock, it should be understood by one skilled in the art that the second connecting mechanism 32 may include any other securing mechanism sufficient to securely connect the first connector 12 to a corresponding tube 24 or passageway including, but not limited to, a male luer lock, friction fit connector, protrusion-detent mechanism, keyed connector, or the like. The connection between the tube 24 and the second connector 14 should be a sealed connection, wherein no fluid or air is introduced into the tube 24 or transducer protector 10 through the seal between the tube 24 and the second connector 14. It should also be understood by one skilled in the art that the first and second connecting mechanisms 18, 32 may be identical types of connecting mechanisms, or in the alternative, the first and second connecting mechanisms 18, 32 may be different types of connecting mechanisms.

In an embodiment, the second securing portion 34 of the second connector 14 extends from the second connecting mechanism 32 and includes a web 42 and a flange 44, as shown in FIGS. 3 and 4. The web 42 extends radially from the second connecting mechanism 32 in a generally perpendicular manner. The flange 44 extends from the web 42 in a generally perpendicular manner such that the flange 44 is aligned in a substantially parallel manner relative to the second connecting mechanism 32. The flange 44 forms a generally cylindrical body extending from the second connecting mechanism 32, but it should be understood by one skilled in the art that the flange 44 may be formed of any shape sufficient to provide a cavity therewithin through which a fluid passes. The second securing portion 34 and the second connecting mechanism 32 surround a second passageway 36 in a generally concentric manner.

In an embodiment, the second passageway 36 is formed in the second connector 14 and is in fluid communication with a tube 24 that is attached to the second connecting member 32, as illustrated in FIGS. 3 and 4. The second passageway 36 extends inwardly from a distal end of the second connector 14. The diameter of the second passageway 36 is constant along the entire length of the second connecting mechanism 32, but it should be understood by one skilled in the art that the diameter may increase, decrease, as desired as the second passageway 36 extends from the distal end of the second connector 14. It should also be understood that the diameter of the second passageway 36 may be the same or different than the diameter of the first passageway 22 of the first connector 12. The second passageway 36 extends through the second connecting mechanism 32 into the second securing portion 34 of the second connector 14.

In an embodiment, the first passageway 22 and the second passageway 36 are in fluid communication, as illustrated in FIGS. 3 and 4, such that fluid passing through the transducer protector 10 enters through the first passageway 22 and exits through the second passageway 36. In an embodiment, the first passageway 22 provides an inlet 46 into the transducer protector 10, and the second passageway 36 provides an outlet 48 out of the transducer protector 10. The flow path, as indicated by arrow F, provides for a fluid to flow in through the first connector 12 and out through the second connector 14. In a further embodiment, the first connector 12 includes a plurality of inlets 46 formed therein. In another embodiment, the second connector 12 includes a plurality of outlets 48 formed therein.

Figure 7:
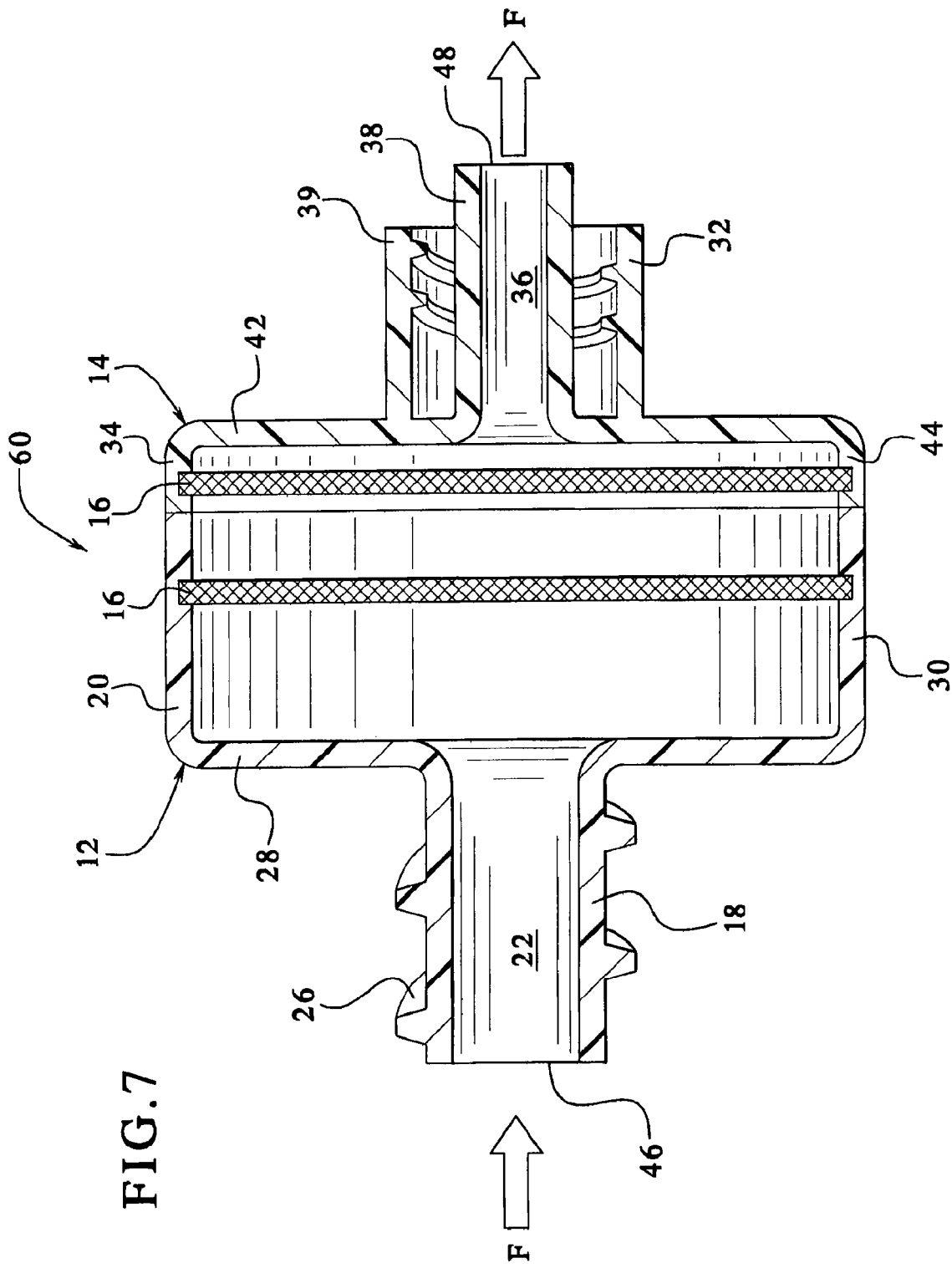
FIG. 7 is a cross-sectional view of yet another embodiment of a transducer protector.

The illustrated embodiment includes at least one membrane 16 disposed between the inlet 46 and outlet 48 through which fluid passes. FIGS. 3 and 4 illustrate an exemplary embodiment of a transducer protector 10 having a single membrane 16 located between the first and second passageways 22, 36. FIG. 7 illustrates another exemplary embodiment of a transducer protector having two membranes 16 in series located between the first and second passageways 22, 36. Additional membranes in series may be used. The membrane 16 separates the inlet 46 and outlet 48 such that any fluid that is transferred through the transducer protector 10 must pass through, or be stopped by, the membrane 16. In an embodiment, the membrane 16 is circular, but it should be understood by one skilled in the art that the membrane 16 may be any shape sufficient to extend between each of the inner surfaces of a flange 30, 44 and to separate the first and second passageways 22, 36.

The transducer protector 10 is in continuous contact with at least one fluid, such as air, which is allowed to transfer the membrane 16 while preventing other fluids, such as water, blood, or other contaminants, from passing therethrough. The membrane 16 is not necessarily in continuous contact with any fluids other than air. In an embodiment, the membrane 16 is hydrophobic, which allows air to pass therethrough but prevents liquids from passing therethrough. In an exemplary embodiment, the membrane 16 prevents blood and blood components from passing therethrough. The seal between the outer periphery of membrane 16 and the housing is desirably hermetic and very secure. It should be understood by one skilled in the art that in addition to blood, other fluids or liquids are also prevented from passing through the membrane 16. The membrane 16 is made of a material that can be washed or disinfected after a treatment with standard disinfecting fluids and with fluids having an elevated temperature. However, one-time only medical use is recommended.

In another embodiment, as shown in FIG. 7, two membranes are aligned in series such that one membrane 16 prevents liquid from passing therethrough and the other membrane 16 is provided as a secondary protective layer in case the first membrane fails or is damaged.

An example of a hydrophobic membrane sufficient for a transducer protector 10 is formed of polytetrafluoroethylene ("PTFE") on a polyester grid. Other hydrophobic membranes that prevent passage of water and blood include polyvinylidenefluoride (PVDF), polyethylene, and polypropylene. The membrane 16 allows air to pass therethrough while preventing water, blood, dialysate, and other liquids from passing therethrough. However, if the transducer protector 10 becomes full of blood or other fluid prevented from passing through the membrane 16, air may likewise be prevented from passing through the transducer protector 10 such that the transducer protector 10 needs to be immediately replaced in order to restore proper fluid flow through the transducer protector 10 for the proper functioning of the pressure transducer. Hydrophobic membranes are available from at least Millipore Corp., Bedford, Mass., U.S.A., and also from W.L. Gore & Assoc., Newark, Del., U.S.A.

In an embodiment, the first connector 12 includes a membrane 16 extending inwardly from the flange 30, wherein the membrane 16 is integrally connected to the first connector 12, as shown in FIGS. 3 and 4. The membrane 16 is integrally attached to the first connector 12 by overmolding the first connecting mechanism 18 and the first securing portion 20 as a single body around the membrane 16 such that the first connector 12 and the membrane 16 form a unitary member. The first connector 12 is formed of polyvinylchloride ("PVC"). However, it should be understood by one skilled in the art that the first connector 12 may be made of any other material sufficient to be overmolded to the membrane 16 as well as be chemically inert with respect to the fluid within the transducer protector 10. It should be understood by one skilled in the art that the first connecting mechanism 18 and the first securing portion 20 may be overmolded as a single body around membrane 16 such that the transducer protector 10 contains at least one membrane 16 for preventing cross-contamination with subsequent patients.

Overmolding the embodiment of FIGS. 3 and 4, e.g., overmolding second connector 14 to the already assembled first connector 12 and membrane 16, may be difficult because once the transducer protector 10 is overmolded, it will be difficult to remove the mold. Accordingly, molding may be more readily accomplished by low-pressure processes that allow relatively soft mandrels, or pieces of mandrels, for the overmolding. For example, rotational molding of PVC could be accomplished with internal pressure bags or an internal mandrel made from several pieces. The pressure bag or internal mandrel should be treated for easy release from the molded transducer protector housing.

In an embodiment, the first connector 12 is overmolded with at least one membrane 16 to form a one-piece member that is separate from the second connector 14, as illustrated in FIGS. 3 and 4. The first connector 12 and membrane 16 provide an inlet 46 and a particular locking mechanism for the transducer protector 10. One advantage of forming the first connector 12 and at least one membrane 16 as a unitary member is that the first connector 12 and integrally attached membrane 16 provide a specific locking mechanism and membrane type for the inlet 46 of the transducer protector 10, while allowing a variety of different configurations of second connectors 14 to be attached thereto.

Once the first connector 12 is formed as a unitary member with the membrane 16, the transducer protector 10 is assembled by attaching the unitary first connector 12 and membrane 16 to a second connector 14, as illustrated in FIGS. 3 and 4. In an embodiment, the second connector 14 includes a membrane 16 connected thereto, as illustrated in FIG. 7. In another embodiment, the second connector 14 does not include a membrane 16 connected thereto, as illustrated in FIGS. 3 and 4. In an embodiment, the first connector 12 is formed of the same material as the second connector 14. In another embodiment, the first connector 12 is formed of a dissimilar material with respect to the second connector 14. In an embodiment, the flange 30 of the first connector 12 is secured to the flange 44 of the second connector 14 by heat welding the flange 30 of the first connector 12 to the flange 44 of the second connector 14, thereby forming a hermetic seal between the first and second connectors 12, 14. A hermetic seal is one which is virtually impervious and does not allow leakage.

In another embodiment, the first connector 12 is attached to the second connector 14 by adhering the flanges 30, 44 together using a medically-acceptable adhesive, such as a medical-grade cyanoacrylate. Bonding may also be accomplished with a solvent bonding agent, such as cyclohexanone or the like. However, it should be understood by one skilled in the art that the first connector 12 may be attached to the second connector 14 by laser welding, sonic welding, radio frequency ("RF") welding, or any other method of fixedly attaching the first connector 12 to the second connector 14 to form a hermetic seal therebetween.

Figure 5:
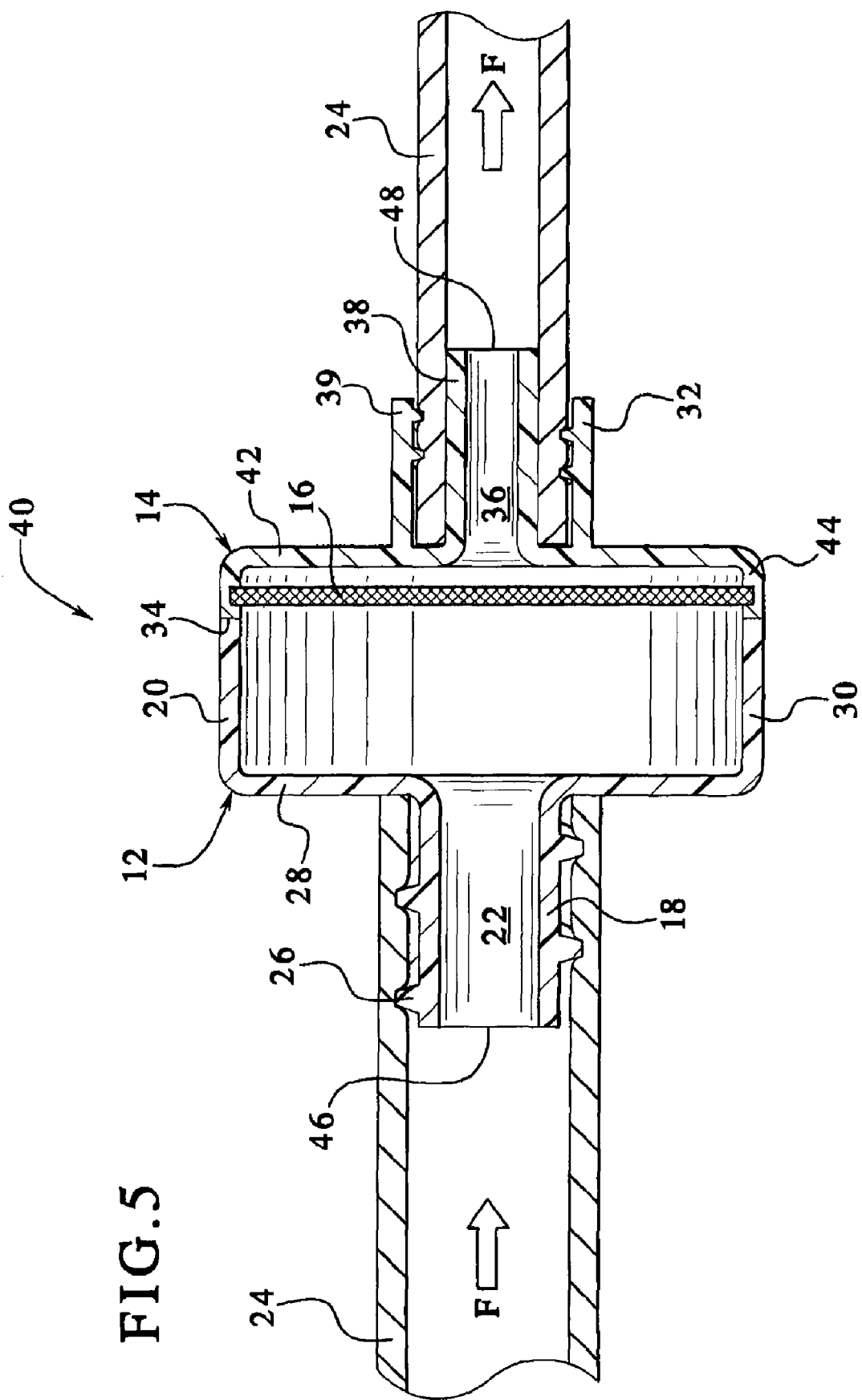
FIG. 5 is a cross-sectional view of a further embodiment of a transducer protector.
Figure 6:
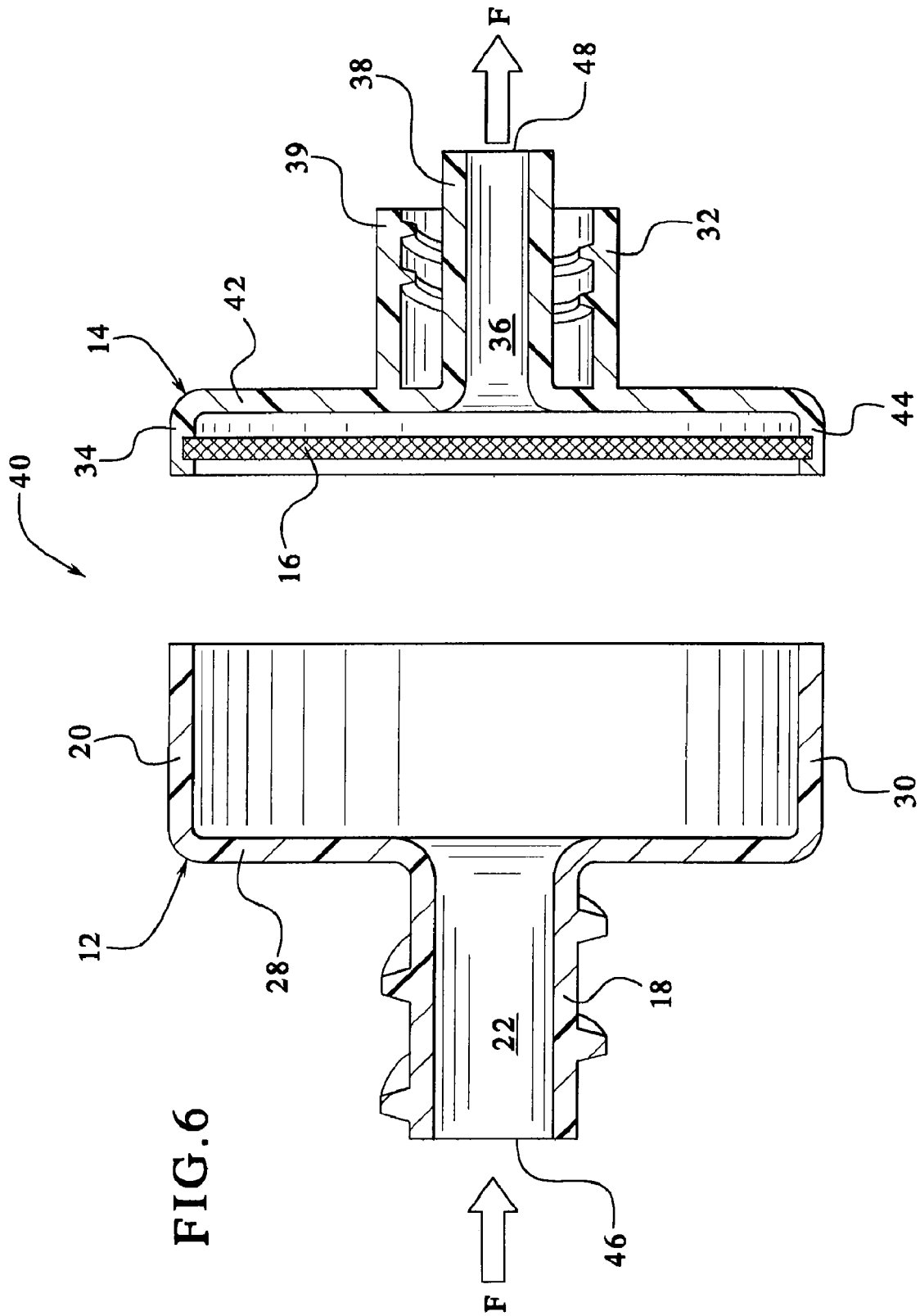
FIG. 6 is an exploded cross-sectional view of the transducer protector of FIG. 5.

In another transducer protector embodiment 40, the second connector 14 includes a membrane 16 extending inwardly from the flange 44, wherein the membrane 16 is integrally attached to the second connector 14, as shown in FIGS. 5 and 6. The membrane 16 is integrally attached to the second connector 12 by overmolding the second connecting mechanism 32 and the second securing portion 34 as a single body around the membrane 16 such that the second connector 14 and the membrane 16 form a unitary member. The second connector 14 is formed of polyvinylchloride ("PVC"). However, it should be understood by one skilled in the art that the second connector 14 may be made of any other material sufficient to be overmolded to the membrane 16 as well as be chemically inert with respect to the fluid contacting the transducer protector 40. It should be understood by one skilled in the art that the second connecting mechanism 32 and the second securing portion 34 may be overmolded as a single body around any number of membranes 16 such that the transducer protector 40 contains at least one, but may also contain a plurality of, membranes 16 for preventing cross-contamination with subsequent patients.

It may be preferable to allow more space on the blood side of the membrane and less space on the pressure transducer side of the membrane. The pressure transducer will be more responsive to pressure changes if the "free" volume on the transducer side is smaller and thus more subject to rapid changes in the pressure from the arterial or venous blood. Accordingly, as can be readily seen in at least FIGS. 4 and 6, the volume on the inlet or blood side of the membrane is less than the volume on the outlet or pressure transducer side. In such an embodiment, the distance from the membrane to the web or larger portion of the inlet housing is longer than the distance from the membrane to the web or larger portion of the outlet housing.

In another transducer protector 40, the second connector 14 is overmolded with at least one membrane 16 to form a one-piece member that is separate from the first connector 12 as illustrated in FIGS. 5 and 6. The second connector 14 and membrane 16 provide an outlet 48 and a particular locking mechanism for the transducer protector 40. An advantage of forming the second connector 14 and at least one membrane 16 as a unitary member is that the second connector 14 and integrally attached membrane 16 provide a specific locking mechanism and membrane type for the outlet 48 of the transducer protector 40, while allowing a variety of different configurations of first connectors 12 to be attached thereto.

Once the second connector 14 is formed as a unitary member with the membrane 16, the transducer protector 40 is assembled by attaching the second connector 14 and membrane 16 to the first connector 12, as illustrated in FIGS. 5 and 6. In an embodiment, the flange 44 of the second connector 14 is secured to the flange 30 of the first connector 12 by heat welding the flange 44 to the flange 30. In another embodiment, the second connector 14 is attached to the first connector 12 by gluing the flanges 30, 44 together using a solvent bonding agent, such as cyclohexanone or the like. However, it should be understood by one skilled in the art that the second connector 14 may be attached to the first connector 12 by laser welding, sonic welding, RF welding, or any other method of fixedly attaching the second connector 14 to the first connector 12 to form a hermetic seal therebetween.

Integrally forming at least one membrane 16 with the first connector 12 or the second connector 14 to form a unitary member provides the membrane 16 with a secure connection to the transducer protector 40, thereby completely separating the first passageway 22 from the second passageway 36 when the transducer protector 40 is assembled. Overmolding the first or second connector 12, 14 to the membrane 16 ensures that the entire outer surface of the membrane 16 is secured to the inner surface of the first or second connector 12, 14 such that there are no gaps between the membrane 16 and the surrounding flange 30, 44. Accordingly, the occurrence of leakage of fluid between the outer edge of membrane 16 and the inner surface of the first or second connector 12 is reduced or eliminated. Overmolding at least one membrane 16 to the first or second connectors 12, 14 also provides an integral connection between the membrane 16 and one member of the transducer protector 40 in a two-piece assembly, wherein the membrane 16 is integrally formed with one of the two pieces prior to the attachment of the two pieces. Assembly of the two-piece transducer protector 40 with an integrally attached membrane 16 eliminates the clamping or holding of a membrane 16 between the first and second connectors 12, 14 as the first and second connectors 12, 14 are bonded together.

In another embodiment, a transducer protector 60 includes a first connector 12 that has a first membrane 16 integrally attached thereto and a second connector 14 that likewise includes a second membrane 16 integrally attached thereto, as illustrated in FIG. 7. In an embodiment, the membranes 16 are both configured to filter the same particular fluids, thereby providing a redundant filter for the transducer protector 60. In another embodiment, one of the membranes 16 filters particular fluids and the second membrane 16 provides a filter for viruses, bacteria or other blood components that are hazardous to successive patients. It should be understood by one skilled in the art that the first and second connectors 12, 14 may be connected to form a transducer protector 60 having various properties for filtering fluids and other blood components dependent upon the types of membranes 16 integrally formed with the first connector 12 and/or second connector 14.

Figure 8:
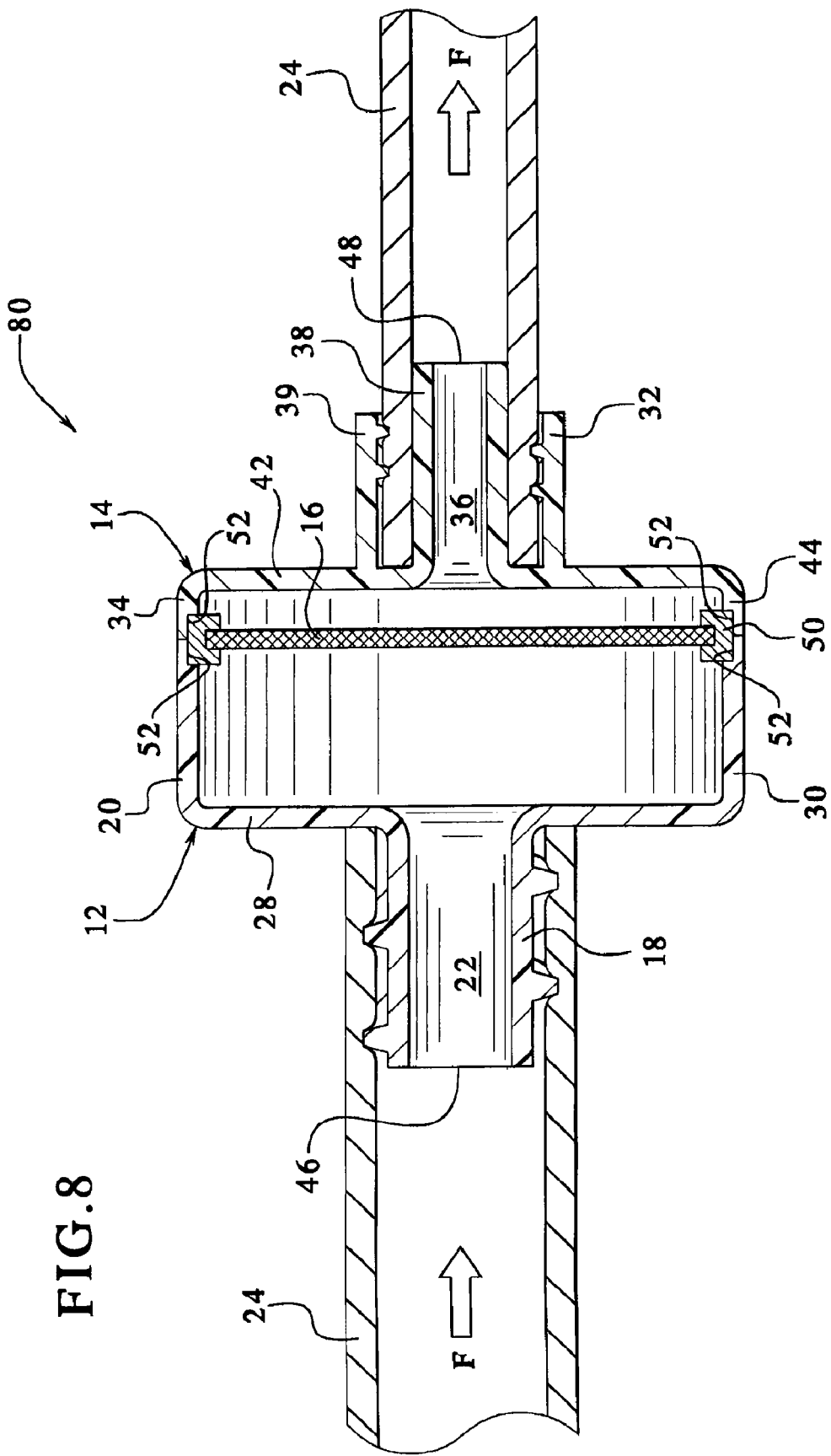
FIG. 8 is a cross-sectional view of yet another embodiment of a transducer protector.
Figure 9:
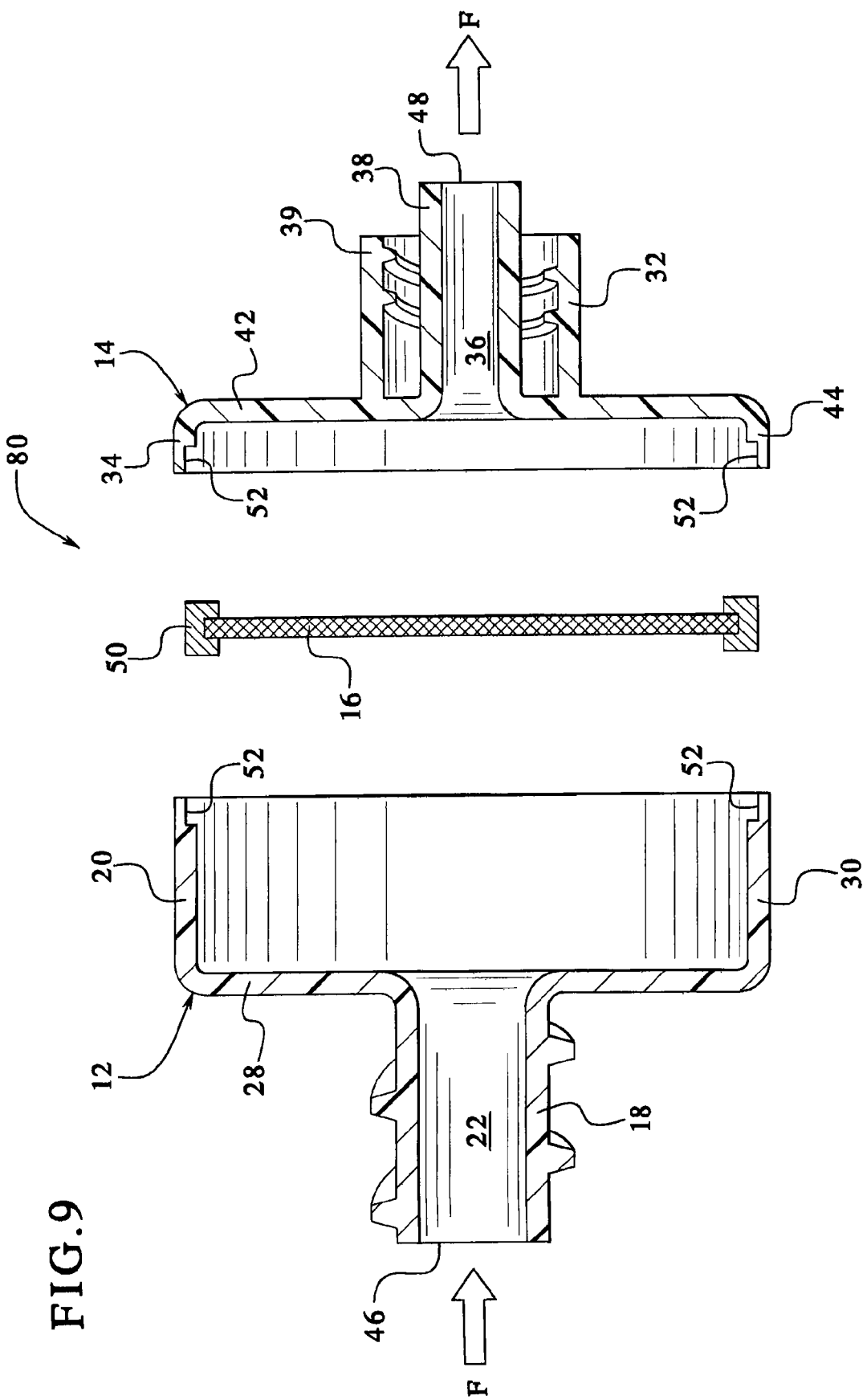
FIG. 9 is an exploded cross-sectional view of the transducer protector of FIG. 8.

In another embodiment of a transducer protector 80, a ring 50 extends around the entire outer surface or periphery of membrane 16 and is integrally connected thereto, as shown in FIGS. 8 and 9. The membrane 16 is integrally attached to the ring 50 by overmolding the ring 50 around the membrane 16 such that the ring 50 and the membrane 16 form a unitary member. The ring 50 is be formed of PVC. However, it should be understood by one skilled in the art that the ring 50 may be made of any other material sufficient to be overmolded with the membrane 16 as well as be chemically inert with respect to the fluid contacting the transducer protector 80. In an embodiment, the first and second connectors 12, 14 are formed of the same material as the ring 50. In another embodiment, the first connector 12 is formed of the same material as the ring 50 but the second connector 14 is made of a dissimilar material relative to the first connector 12 and the ring 50. In another embodiment, the second connector 14 is formed of a the same material as the ring 50 but the first connector 12 is made of a dissimilar material relative to the second connector 14 and the ring 50. In another embodiment, the first connector 12, second connector 14, and the ring 50 are each formed of dissimilar materials.

Once the ring 50 is formed as a unitary member with the membrane 16, the transducer protector 80 is assembled by attaching the first connector 12, second connector 14, and membrane 16 together, as illustrated in FIGS. 8 and 9. In an embodiment, the outer diameter of the ring 50 is smaller than the outer diameter of the flange 30 of the first connector 12 as well as the flange 44 of the second connector 14. Each flange 30, 44 includes a shoulder 52 formed along the inner surface at the outer edge thereof. The shoulders 52 receive the ring 50. When assembled, the ring 50 is disposed within the first and second connectors 12, 14 such that the ring 50 is in an abutting relationship with the opposing shoulders 52 and the flanges 30, 44 are in a similar abutting relationship. The ring 50 is securely attached to the shoulders 52. The flange 30 of the first connector 12 is securely attached to the flange 44 of the second connector 14 to form a hermetic seal therebetween.

In another embodiment (not shown), the outer diameter of the ring 50 is the same as the outer diameter of the flange 30 of the first connector 12 as well as the flange 44 of the second connector 14, wherein the ring 50 is located between the flanges 30, 44 of the first and second connectors 12, 14 in an abutting, sandwiched manner, and wherein the outer surfaces of the first connector 12, ring 50, and second connector 14 are substantially planar. In another embodiment, the outer diameter of the ring 50 is substantially the same size as the inner diameter of the flange 30 of the first connector 12 or the flange 44 of the second connector 14 such that the ring 50 is attached to the inner surface of the flange 30 of the first connector 12 or the inner surface of the flange 44 of the second connector 14 prior to the attachment of the first and second connectors 12, 14 to form a hermetic seal therebetween.

In an embodiment, the flange 30 of the first connector 12, the ring 50, and the flange 44 of the second connector 14 is attached by heat welding the flanges 30, 44 to opposing sides of the ring 50. In another embodiment, the first connector 12, second connector 14, and the ring 50 are attached by gluing the flanges 30, 44 to opposing sides of the ring 50 using a solvent bonding agent, such as cyclohexanone or the like. However, it should be understood by one skilled in the art that the first connector 12, second connector 14, and ring 50 may be attached via any of the methods described herein.

Figure 10:
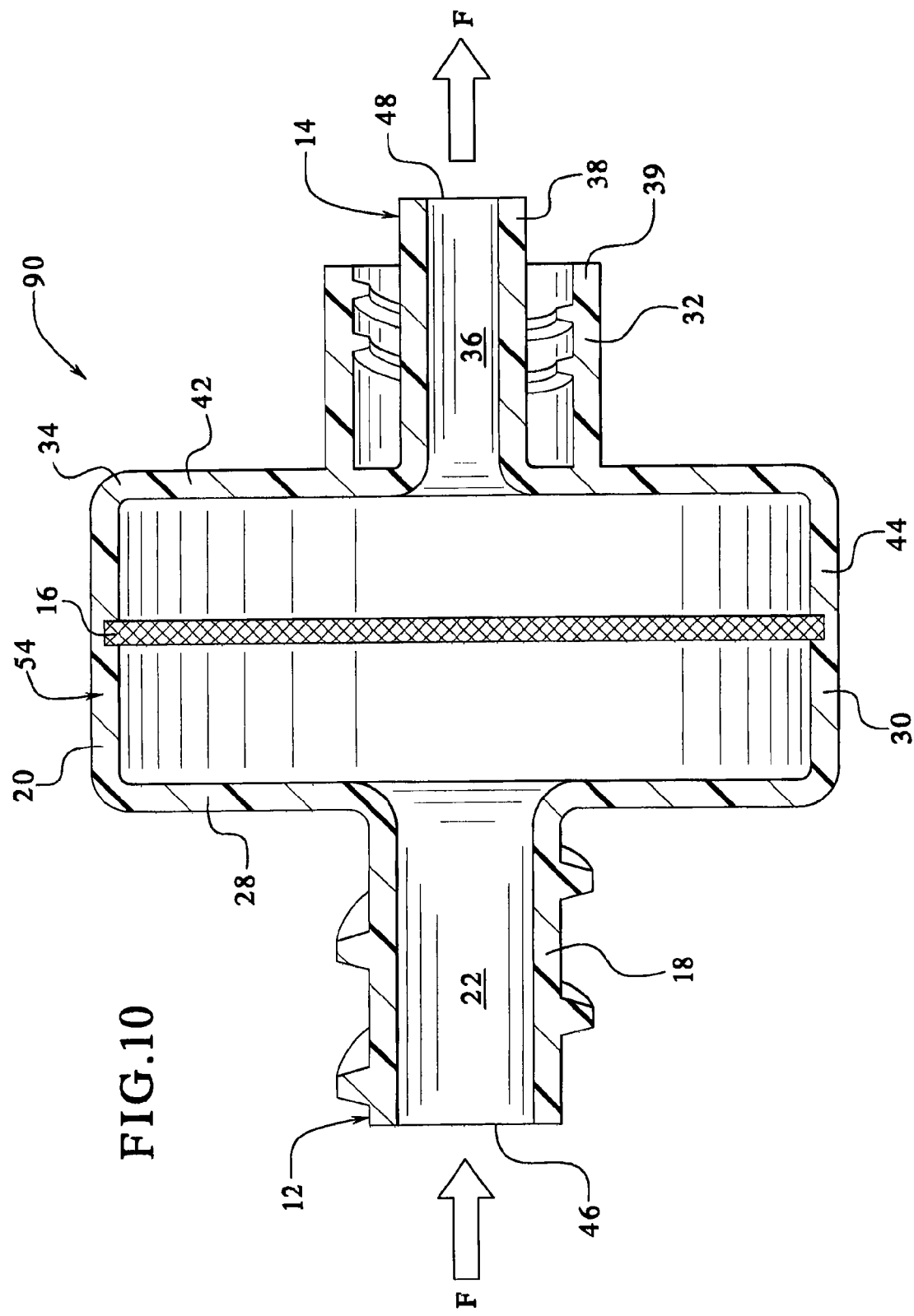
FIG. 10 is a cross-sectional view of still a further embodiment of a transducer protector.

In another embodiment of a transducer protector 90, the first connector 12 and the second connector 14 are formed together as a single housing 54 that surrounds at least one membrane 16, as illustrated in FIG. 10. The housing 54 is formed of a moldable material that may be any one or more of, but is not limited to, polyvinylchloride (PVC), polyamide or nylon (PA), polycarbonate (PC), polyethylene (PE), polypropylene (PP), acrylonitrile-butadiene-styrene (ABS). The housing 54 is integrally attached to the membrane 16 by overmolding the housing 54 as a single body to the membrane 16, thereby forming a unitary, one-piece transducer protector 90. The housing 54 includes a first connector 12, second connector 14, and a membrane 16. The first connector 12 includes a first connecting mechanism 18 and a first securing portion 20. The second connector 14 includes a second securing portion 34 and a second connecting mechanism 32. The housing 54, which includes the first and second connectors 12, 14, is formed of PVC. However, it should be understood by one skilled in the art that the housing 54 may be made of other materials that are capable of being overmolded to at least one membrane 16 in addition to being chemically inert with respect to the fluid contacting the transducer protector 90.

The membrane 16 is integrally formed with the housing 54 as a one-piece, unitary transducer protector 90 to provide the membrane 16 with a secure connection to the housing 54, thereby completely separating the first passageway 22 from the second passageway 36. The housing 54 is overmolded to the membrane 16 to ensure that the entire outer surface of the membrane 16 is secured to the inner surface of the housing 54 such that there are substantially no gaps formed between the membrane 16 and the housing 54. Overmolding the housing 54 with the membrane 16 reduces or eliminates the occurrence of leakage of fluid between the outer edge of membrane 16 and the inner surface of the housing 54. Overmolding the membrane 16 with the housing 54 reduces the amount of assembly of parts, thereby further eliminating potential leakages between the housing 54 and the membrane 16 and providing a hermetically sealed fluid path F within the transducer protector 90. The one-piece transducer protector 90 eliminates the need for further assembly of parts to form the transducer protector 90, thereby reducing the overall cost of assembly as well as costs associated with storing multiple parts that require additional assembly.

The process of overmolding the first connector 12, the second connector 14, the ring 50, or the housing 54 to at least one membrane 16 is done by molding in which the membrane 16 is placed within a mold (not shown) into which the material forming the first connector 12, second connector 14, ring 50, or housing 54 is injected or placed, thereby integrally attaching the first connector 12, the second connector 14, the ring 50, or the housing 54 to the membrane 16. Integrally forming the membrane 16 with the first connector 12, second connector 14, ring 50, or housing 54 reduces the number of parts to be assembled to form the finished transducer protector 90 while ensuring the membrane 16 forms a substantially complete seal between the first and second passageways 22, 36. As noted above, molding transducer protector 90 in a single overmolding process may be technically challenging, and processes requiring softer or removeable internal tooling may be preferred.

Figure 11:
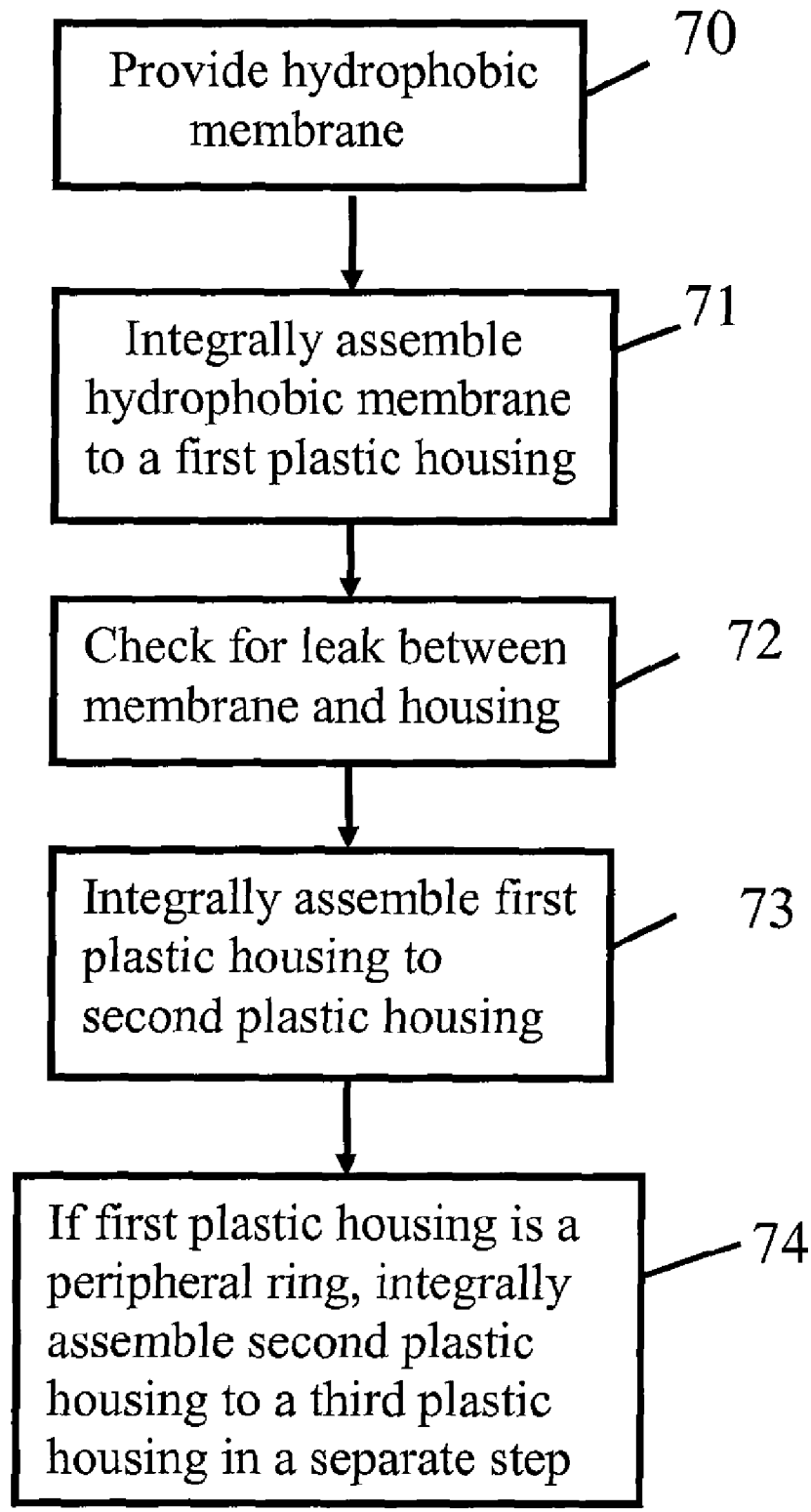
FIG. 11 is a flow chart for a method of making a transducer protector.

A process for a method of making a transducer protector is depicted in the flow chart of FIG. 11. In this process, a first step 70 is to provide a hydrophobic membrane. The hydrophobic membrane is integrally assembled 71 to a first plastic housing. Optionally, but preferably, the seal formed by the integral assembly is checked 72 for leaks. This will insure that no blood can leak around the membrane when a patient is undergoing a dialysis procedure. The first plastic housing with the membrane is than integrally assembled 73 to a second plastic housing. If there are only two plastic parts, one with an inlet and one with an outlet connector, the assembly may be complete. However, if the first plastic housing was a peripheral ring, it will be necessary to complete the assembly 74 of the transducer protector by integrally assembling the second plastic housing, preferably having an inlet connector, to a third plastic housing, preferably having an outlet connector.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A transducer protector for use in a blood treatment therapy, the transducer protector comprising:
    a first connector having an inlet passageway for receiving at least one fluid;
    a second connector having an outlet passageway opposing the inlet passageway, the second connector being attached to the first connector; and
    a hydrophobic membrane integrally assembled with one of the first connector and the second connector, so that an entire outer radial surface of the hydrophobic membrane is integrally attached to and surrounded by an inner surface of one of the first and the second connectors to form a unitary member, the hydrophobic membrane separating the inlet passageway from the outlet passageway, wherein the first and second connectors form an integrally-connected housing for protecting the hydrophobic membrane.

2. The transducer protector of claim 1, wherein the hydrophobic membrane is integrally assembled to the first or second connector by a process selected from the group consisting of adhesive bonding, solvent bonding, heat welding, laser welding, sonic welding, and radio frequency ("RF") welding.

3. The transducer protector of claim 1, wherein one of the first connector and the second connector are attached to the hydrophobic membrane by overmolding.

4. The transducer protector of claim 1 wherein a volume of the housing from the hydrophobic membrane to the inlet passageway is greater than a volume of the housing from the hydrophobic membrane to the outlet passageway.

5. The transducer protector of claim 1, wherein the first connector is attachable to the second connector by a process selected from the group consisting of adhesive bonding, solvent bonding, heat welding, laser welding, sonic welding, and radio frequency ("RF") welding.

6. The transducer protector of claim 1, wherein the hydrophobic membrane and the first or second connector form a hermetic seal.

7. The transducer protector of claim 1, wherein the first connector includes a first connecting mechanism and the second connector includes a second connecting mechanism.

8. The transducer protector of claim 7, wherein one of the first connecting and the second connecting mechanism is a male Luer lock or a female Luer lock.

9. The transducer protector of claim 1, wherein the hydrophobic membrane is made from a material selected from the group consisting of fluoropolymers, polytetrafluoroethylene, polytetrafluoroethylene on a polyester grid, polyethylene, ultra high molecular weight polyethylene, and polyvinylidenefluoride.

10. The transducer protector of claim 1, further comprising a second hydrophobic membrane mounted in series with the hydrophobic membrane, the second hydrophobic membrane integrally formed with the other of the first and second connectors.

* * * * *